United States Patent [19]

Watanabe et al.

[11] Patent Number: 4,980,038

[45] Date of Patent: Dec. 25, 1990

[54] COSMETIC AND METHOD FOR PRODUCTION THEREOF

[76] Inventors: Shizuho Watanabe, 39-5 Kugayama 3-chome, Suginami-ku, Tokyo; Shigenobu Fujimoto, 462-19, Fueda, Kamakura-shi, Kanagawa-ken, both of Japan

[21] Appl. No.: 258,597

[22] Filed: Oct. 17, 1988

[51] Int. Cl.$^5$ ............................................. B01J 19/08
[52] U.S. Cl. ............................... 204/157.15; 366/348; 514/844; 514/846
[58] Field of Search .................. 204/157.15; 366/348; 514/844–848

[56] References Cited

FOREIGN PATENT DOCUMENTS 61-21163  2/1986  Japan .

*Primary Examiner*—T. Tung
*Assistant Examiner*—Ben C. Hsing
*Attorney, Agent, or Firm*—Ronald P. Kananen

[57] ABSTRACT

A cosmetic of stable quality is produced by a method which comprises applying superposed electric waves severally on an aqueous part and an alcohol part or an oil part, then mixing the aqueous part with the alcohol part and/or the oil part, and subsequently applying the superposed electric waves on the resultant mixture. By this method, in spite of the absence of a surface active agent, the aqueous part and the alcohol part and/or the oil part are uniformly dissolved, dispersed, or emulsified in each other to produce a cosmetic lotion, a cosmetic milky lotion, or a cosmetic cream which remains stably for a long time.

12 Claims, 2 Drawing Sheets

COSMETIC AND METHOD FOR PRODUCTION THEREOF

BACKGROUND OF THE INVENTION

1. Field of the Invention

This invention relates to novel cosmetics, particularly cosmetics such as lotions, milky lotions, and creams which contain no surface active agent, and to a method for production of the cosmetics.

2. Description of the Prior Art

The cosmetics are generally classified under three major kinds, i.e. lotions, milky lotions, and creams. The lotions consist exclusively of an aqueous part and an alcohol part. The alcohol part incorporates therein a surface active agent for the purpose of ensuring uniform solution of an oil component to be used for preventing the aqueous part from being volatilized. In contrast, milky lotions and creams consist exclusively of an aqueous part and an oil part and require a surface active agent for ensuring emulsification.

When the surface active agent contained in a cosmetic comes into contact with the human skin, it induces a defatting action and degenerates keratoproteins and eventually chaps the skin. It induces one of the serious problems for cosmetics, often irritating the skin, the mucous membrane, and the like and, in an extreme case, inflicting scarlet itchy spots on the region of contact. Various attempts have been made to decrease the amount of the surface active agent to be used to the fullest possible extent or, more desirably, to eliminate the use thereof completely. For a cosmetic to be retained stably in the form of a uniform solution or emulsion for a long time, however, the use of a surface active agent has been an inevitable requirement.

SUMMARY OF THE INVENTION

A main object of this invention, therefore, is to provide cosmetics containing no surface active agent and a method for the production of such cosmetics.

Another object of this invention is to provide cosmetics which are enabled to retain the state of a uniform solution or emulsion stably for a long time without requiring the use of any surface active agent and a method for the production of such cosmetics.

Yet another object of this invention is to provide cosmetics which are incapable of either irritating the skin, the mucous membrane, and the like or inducing the problem of skin chapping or itching, for example.

To accomplish the objects described above, according to this invention, there is provided a method for the production of a cosmetic, which comprises severally applying superposed electric waves on the aqueous part and the alcohol part or the oil part, then mixing the aqueous part and the alcohol part and/or the oil part, and thereafter applying superposed electric waves again on the resultant mixture.

By this method, the aqueous part and the alcohol part and/or the oil part are uniformly dissolved, dispersed, or emulsified to produce a cosmetic such as, for example, a lotion, a milky lotion, or a cream capable of stably retaining the original state for a long time, despite the total absence of a surface active agent.

The term "aqueous part" as used herein refers to an aqueous solution which has water as a main component and optionally incorporates various additives accepted for cosmetics. By the same token, the term "alcohol part" and the term "oil part" respectively refer to mixtures which have an alcohol and an oil as a main component and optionally incorporate various additives for cosmetics. The term "superposed electric wave" refers to those formed by superposing a high-frequency electric current of medium to long wavelength on a high-frequency electric current of short wavelength.

DETAILED DESCRIPTION OF THE INVENTION

Figure 1:
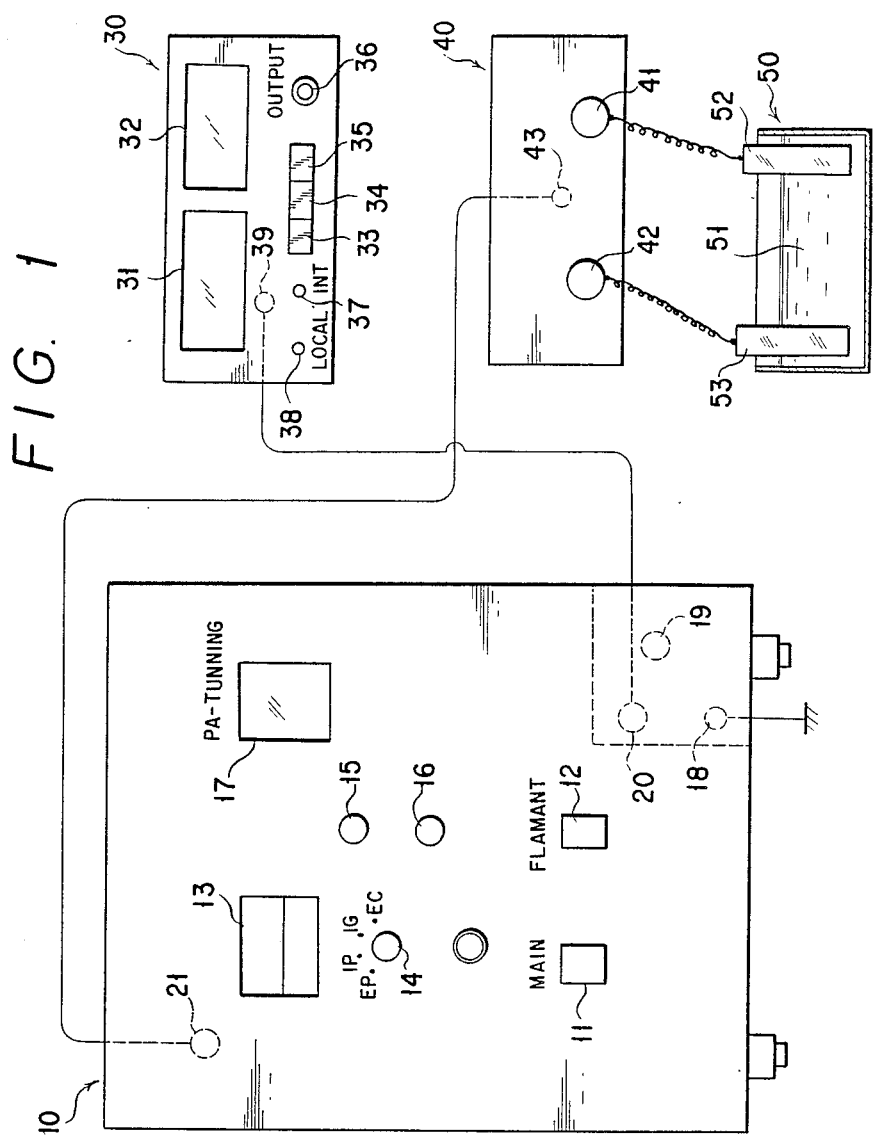
FIG. 1 is a diagram schematically illustrating the overall appearance of a typical apparatus for the application of superposed electric waves on a mixture under treatment, as one embodiment of this invention.
Figure 2:
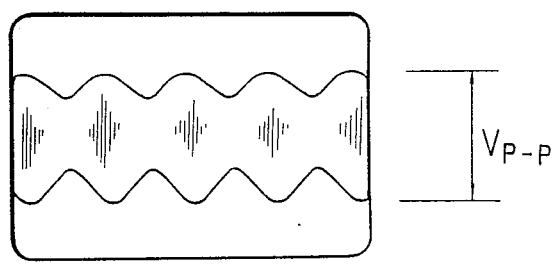
FIGS. 2 to 5 are schematic diagrams illustrating examples of the typical waveforms of various superposed electric waves generated by a superposed electric wave generating apparatus.
Figure 3:
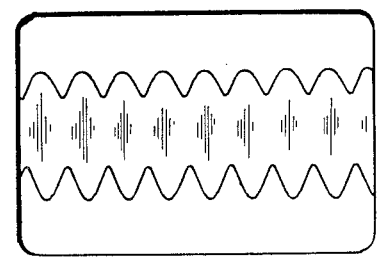
Figure 4:
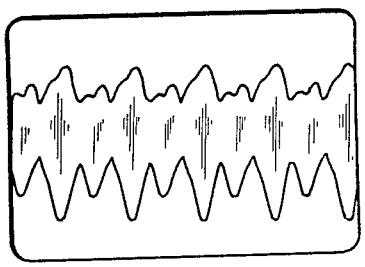
Figure 5:
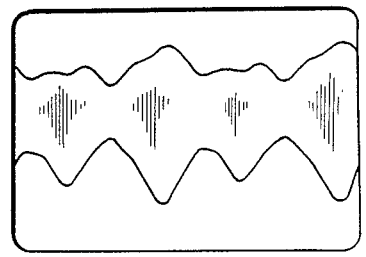

Generally when an aqueous solution and a mixture containing a water-insoluble oil part are mixed and uniformly dispersed in each other, the resultant dispersion separates into an aqueous phase and an oil phase after standing at rest for a short time. In the production of a cosmetic, therefore, it has been customary to use a surface active agent. This use of the surface active agent has entailed the various drawbacks mentioned above.

Surprisingly, the inventors's study has ascertained that even in the absence of a surface active agent, a lotion, a milky lotion, or a cream, having an aqueous part which is the main component of the cosmetic, and an alcohol part containing oil or an oil part uniformly dispersed or emulsified in each other in suitable proportions, can be obtained by applying superposed electric waves severally on the aqueous part and the alcohol part or the oil part and applying the superposed electric waves on the mixture of the aqueous part with the alcohol part and/or the oil part and that the produced cosmetic can stably retain the state of uniform dispersion or emulsion for a long time. Naturally, such water-soluble substances as alcohol readily dissolves in the aqueous phase.

As the aqueous part, a purified water or a deionized water is generally used. It is particularly desirable to use the constant-pH water which is disclosed in the specification of Japanese Patent Publication No. SHO 61(1986)-21,163 issued to one of the inventors hereof. This constant-pH water is obtained by causing a purified water obtained by treating the water with an ion-exchange resin and/or activated carbon to absorb an ozone-containing air obtained by passage through a high-voltage electron discharge apparatus. The constant-pH water possesses a pH value approximately in the range of 7.5 to 8.0 and a dissolved oxygen content approximately in the range of 8 to 11 ppm. It manifests the constant-pH property, i.e. the nature of resuming the original pH value after the pH value has been altered by some external factor. It exhibits an outstanding efficacy as in softening the corneal stratum of the skin, activating the metabolism of the skin, enhancing the circulation of blood in the skin, and normalizing the cutaneous function. This constant-pH water, therefore, can be used particularly advantageously as the aqueous part of cosmetics contemplated by the present invention. Passages of the aforementioned specification which are pertinent hereto are incorporated in the present specification by way of reference.

Generally, ethanol is employed as an alcohol to be used as the alcohol part herein.

Any of all the oils designated as acceptable for cosmetics in the Legal Standard for Cosmetics can be employed as the oil part in this invention. As concrete examples of such oils, vegetable oils such as olive oil, corn oil, safflower oil, and jojoba oil (oil of cactus); animal fats such as whale oil, lanolin, beeswax, and squalane; mineral oils such as liquid paraffin, vaseline, and microcrystalline wax; and fatty acids such as stearic acid, myristic acid, and lauric acid may be mentioned.

Any of the oils designated above can be employed as the oil part to be uniformly mixed in the alcohol part as in lotions. Any of the oils enumerated above can be employed.

Optionally, various additives may be incorporated into the aqueous part, the alcohol part, the oil part, or the mixture of such parts to be used in the present invention in order to secure or improve the characteristic property of the cosmetic obtained. As concrete examples of such additives, paraben type antiseptics such as methyl, butyl, and propyl paraoxybenzoates; antioxidants such as vitamin E, thickening agents or touch improvers such as carboxy vinyl polymers and xanthene gum; allergy-mitigating agents such as liver extract and dipotassium glycyrrhetate; dyes such as Red 2 and Blue 1; various perfumes; humectant such as 1,3-butylene glycol, PCA soda (sodium pyrrolidonecarboxylate), glycerin, sodium hyaluronate, and PRODEW (trademark designation); and aloe extract, placental extract, cucumber extract, carrot extract, lithospermum extract, and yolk lecithin may be mentioned.

As regards the proportions of the aqueous part, the oil part, and the alcohol part to be used, the proportion of the alcohol part is in the range of 6 to 20% parts by weight containing an oil in the range of 1 to 10% by weight, based on the total amount of the cosmetic, generally in the case of lotions. Generally in the case of creams, the aqueous part: oil part ratio is in the range of 50-70:50-30. In the case of milky lotions, the aqueous part: oil part ratio is in the range of 80-90:20-10.

The superposed electric waves to be employed in the present invention are those obtained by superposing the high-frequency electric currents on the order of long to medium wavelength ranging from 100 to 3,000 KHz, more desirably 200 to 1,000 KHz, and most desirably 250 to 500 KHz, and those on the order of short wavelength ranging from 25 to 30 MHz, preferably falling in the neighborhood of 27 MHz. These component electric waves can be generated by a suitable oscillating circuit such as, for example, a Colpitts circuit, a Hartley circuit, or an LC circuit. By suitably combining the oscillating circuits, the component electric waves can be converted into superposed electric waves.

In the production of the cosmetics of this invention, these superposed electric waves are first applied severally on the aqueous part, the alcohol part containing an oil, or the oil part and then applied again on the mixture of these parts. The cosmetics as contemplated by this invention are not obtained by applying these superposed electric waves solely on the mixture or solely on each of the component parts prior to the mixture of the component parts.

The application of the superposed electric waves is generally carried out for a period approximately in the range of 5 to 100 minutes per 1 kg of the substance under treatment. The length of the application time increases with the increasing amount of cosmetic materials under treatment.

FIG. 1 illustrates a typical apparatus for application of superposed electric waves as a preferred embodiment of this invention. An superposed electric wave oscillating device denoted generally by reference numeral 10 serves the purpose of generating the superposed electric waves by causing the waveform of the electric waves on the order of the aforementioned medium to long wavelength derived from an external source to apply a high-frequency wave oscillating device. The superposed electric wave oscillating device 10 is provided on the front side thereof with a main switch 11 (power source switch), a FLAMANT switch 12 (for a heater of a vacuum tube), a volt-ammeter 13 for a power amplifier, a changeover switch 14 for the power amplifier, a frequency-adjusting knob 15 for superposed electric waves, a gain-adjusting knob 16 for superposed electric waves, and an impedance-adjusting knob 17. The superposed electric wave oscillating device 10 is provided on the rear side thereof with a grounding terminal 18, an input connector 19, an output connector 20 for a control box, and an output connector 21. The output connector 20 for the control box is connected to a control box input connector 39 which is disposed on the rear side of a control box 30. The output connector 21 is connected to a distributor input connector 43 which is disposed on the rear side of a distributor 40.

The control box 30 is provided on the front side thereof with a power meter 31 for progressive waves, a power meter 32 for reflected waves, a high-voltage power source ON switch (RF-ON switch) 33, a high-voltage power source OFF switch (RF-Off switch) 34, an indicator lamp 35 for indicating troubles, an output adjusting knob 36, an interior-exterior changeover switch 37 (to be used internally), and a REMOTE-LOCAL changeover switch 38 (to be used locally). The output connectors 41 and 42 of the distributor are connected respectively to electrodes 52 and 53 which are made of stainless steel, for example. These electrodes 52 and 53 are kept immersed in a liquid 51 held in an application tank 50.

The apparatus described above begins operating by turning on the main switch 11 and the FLAMANT switch 12. Two to three minutes after the start of the apparatus, the apparatus is connected to the high-voltage power source by turning on the RF-ON switch 33. With the scale reading of the progressive wave meter 31 kept under close watch, the output adjusting knob 36, initially set at the zero point on the lefthand side, is gradually turned clockwise so as to confirm the presence of an output by the detection of a motion of the index of the progressive wave meter 31. Then, the reflected wave meter 32 is examined to find whether or not the index thereof is in motion. The absence of this motion indicates the absence of trouble. When this motion is detected, the electrodes 52 and 53 are moved toward each other so as to decrease the amount of the motion and are then fixed at the positions where the motion is minimum. The reflected waves are of wattless power. After the electrodes have been completely adjusted in position as described above, the output adjusting knob 36 is again turned clockwise to boost the output.

Concerning the adjustment of the superposed electric waves to be applied, the frequency of the waveform of the medium to long wavelength to be superposed on the prescribed short waves of a wavelength in the range of 25 to 30 MHz can be adjusted by manipulation of the frequency-adjusting knob 15. When the superposed electric waves are set at a frequency in the range of 100 to 500 KHz (hereinafter the output of superposed electric waves will be expressed by the frequency of the waveform of superposing), for example, the dial of the knob 15 is calibrated into 100 graduates; the 100th graduation (to be reached when the knob is fully turned clockwise) represents 500 KHz and the first graduation (to be reached when the knob is fully turned counterclockwise) represents 100 KHz. The degree of amplification of the waveform to be superposed can be adjusted by turning the gain-adjusting knob 16. The degree increases as the knob 16 is turned clockwise.

After the superposed electric waves have been applied on the liquid 51 in the application tank 50 for a prescribed time, the output is decreased to zero by turning the output adjusting knob 36 counterclockwise and then turning the FLAMANT switch 12 off. The main switch 11 is turned off about 5 minutes after the vacuum tube has been cooled.

The application of the superposed electric waves severally on the main components of a cosmetic, i.e. the aqueous part and the alcohol part or the oil part, is effected by the procedure described above on each of the component parts. Thereafter, the superposed electric waves are applied again on the mixture of the component parts.

The waveform of the superposed electric waves to be applied can be varied by suitably varying the waveform of the electric waves of the medium to long wavelength to be superposed. A few examples of the waveform are shown in FIGS. 2 to 5. The outer waveform shown in each of the diagrams can be adjusted by the frequency-adjusting knob 15 and the peak-to-peak voltage $V_{p-p}$ by the gain-adjusting knob 16 as described above.

The invention has been described with reference to the operation of the superposed electric wave application apparatus illustrated as a preferred embodiment of the invention in the diagram. This invention is not limited to the description. For the embodiment of this invention, any of can be employed the devices which are capable of generating the superposed electric waves contemplated by this invention.

Now, the present invention will be described more specifically below with reference to working examples, which are merely illustrative, and not in the least limitative, of this invention.

Example 1

This example concerns preparation of a cosmetic cream. An oil part (A) of this cream was obtained by dissolving the following ingredients at a temperature in the range of 60° to 80° C.

| Oil part (A) | |
|---|---|
| Ingredient | Parts by weight |
| Squalane | 18.50 |
| Beeswax | 4.00 |
| Microcrystalline wax | 3.00 |
| Stearic acid | 3.40 |
| Paraoxybenzoate | 0.22 |
| Methylphenyl polysiloxane | 0.20 |
| Behenyl alcohol | 3.10 |
| Jojoba oil (oil of cactus) | 0.30 |
| Natural vitamin E | 0.02 |

-continued

| Oil part (A) | |
|---|---|
| Ingredient | Parts by weight |
| Soybean phospholipid | 2.00 |

In an apparatus constructed as illustrated in FIG. 1, superposed electric waves of about 500 KHz (40 $V_{p-p}$) were applied on the produced oil part for 37 minutes. The superposed electric wave oscillating device used for the application was rated as follows. This device was similarly used in the following examples.

| | |
|---|---|
| Output frequency | 27 MHz |
| Rated output | 500 W |
| Superposed electric wave | 100 KHz–500 KHz |
| Output impedance | 50 Ω |
| Output connector | NR type |
| Method of cooling | Forced air cooling |
| Input power sorce | AC 200 V, 50–60 Hz |

An aqueous part (B) was obtained by dissolving the following components (b-1 to b-3) indicated below under application of heat in a constant-pH oxygen-dissolved water (pH 7.6 and dissolved oxygen content 8.98 ppm), (b-4), also indicated below, prepared in advance by following the procedure of a working example cited in the specification of Japanese Patent Publication No. SHO 61(1986)-21,163. In the same manner as described above, superposed electric waves of about 500 KHz was applied to the aqueous part (B) for 35 minutes.

| | Ingredient | Parts by weight |
|---|---|---|
| | Aqueous part (B) | |
| b-1 | 1,3-Butylene glycol | 5.00 |
| b-2 | Dipotassim glycyrrhetate | 0.10 |
| b-3 | Potassium hydroxide | 0.15 |
| b-4 | constant-pH oxygen-dissolved water | 58.57 |
| | Other additives (C) | |
| c-1 | Sodium hyaluronate | 0.01 |
| c-2 | Humectant liquid (PRODEW ®) | 1.00 |
| c-3 | Human placental liquid | 0.30 |
| c-4 | Formulated perfume | 0.13 |

(The total amount of the oil part (A), the aqueous part (B), and the other additives (C) is 100 parts by weight.)

Then, the aqueous part (B) was mixed with the ingredient (C-1) and the resultant mixture was heated and stirred in the oil part (A). To the stirred mixture, superposed electric waves of about 500 KHz were applied in the same manner as described above for 40 minutes. The resultant mixed liquid was cooled, mixed with the ingredient (c-4) at 60° C., and further mixed with the ingredients (c-2) and (c-3) at 40° C. to produce a cream.

Test for stability

To check the stability of the produced cream mentioned above, samples of the cream were subjected to accelerated tests at high temperature and low temperature to determine degeneration by aging.

1. Test for aging at high temperature

Instrument: Electric constant-temperature drier, 100V, 11KW, 20° to 200° C., produced by Kondo Kagaku Kikai Seisakusho Test conditions 40° C. ±2° C., 60% RH for six months

2. Test for aging at low temperature

Instrument: Refrigerator, 144 liters, 100V 2.2A, produced by Matsushita Electric Industrial Co., Ltd. and marketed under trademark designation of "National NS170 AB".

Test conditions: $-5°$ C. $\pm 2°$ C. for three months.

3. Test items (1) Evaluation of emulsification (diluted at outset of test and evaluated by detection of sign of separation of ingredients after aging)
(2) Determination of pH value
(3) Evaluation of appearance (in terms of hue, viscosity or rigidity, grain size, gloss, and tough)

4. Samples

Creams sampled from a given batch (packed in glass vial). The results are shown in Table 1.

TABLE 1

Test for aging at high temperature: About six months
Test for aging at low temperature: About three months

| | | Evaluation of emulsification | | | Evaluation of appearance | | | | |
|---|---|---|---|---|---|---|---|---|---|
| | Date of check | Dilution | Sign of separation | pH value | Hue | Viscosity or rigidity | Grain size | Gloss | Tough |
| High temperature | April 22, 1985 | done | | 6.62 | | | | | |
| | April 30, 1985 | | | 6.62 | | | | | |
| | May 7, 1985 | | | 6.63 | | | | | |
| | May 31, 1985 | | | 6.62 | | | | | |
| | June 29, 1985 | | | 6.75 | | | | | |
| | July 26, 1985 | | | 6.75 | | | | | |
| | August 30, 1985 | | | 6.85 | Δ | | | | |
| | September 24, 1985 | | | 6.85 | Δ | | | | |
| | October 3, 1985 | | | 6.85 | Δ | | | | |
| Low temperature | April 22, 1985 | done | | 6.62 | | | | | |
| | April 30, 1985 | | | 6.62 | | | | | |
| | May 7, 1985 | | | 6.62 | | | | | |
| | May 31, 1985 | | | 6.63 | | | | | |
| | June 29, 1985 | | | 6.70 | | | | | |
| | July 26, 1985 | | | 6.72 | | | | | |

Scale of rating:
 -Satisfactory
Δ-Slightly degenerated

It is clearly noted from the test results given above that only in the test for aging at high temperature, the samples showed slight signs of pH change and discernible signs of change of hue to yellow. The changes were not serious drawbacks for cosmetics. The other characteristic properties were not altered to any discernible extent. Because the cream used absolutely no emulsifying agent, it neither chapped nor irritated the skin during protracted use.

Example 2

A cosmetic cream was prepared by following the procedure of Example 1, excepting a deionized water was used in the place of the constant-pH oxygen-dissolved water. The cream thus obtained was in the state of uniform emulsion. The cream, after aging, showed a slight sign of pH change. Even after about six months'-standing at rest, it showed absolutely no sign of separation of the oil phase.

Example 3

This example concerns preparation of a cosmetic lotion. An alcohol part (A) of the lotion was prepared by mixing and dissolving the following ingredients in one another. To the alcohol part (A), superposed electric waves of about 400 KHz were applied for 27 minutes.

| Alcohol part (A) | |
|---|---|
| Ingredient | Parts by weight |
| Denatured alcohol (standard: Pharmaceutical Council 295 in Japan - ethanol) | 8.00 |
| Gamma Oryzanol | 0.50 |
| Jojoba oil | 1.50 |
| Sunflower oil | 1.50 |

Separately, an aqueous part (B) was prepared by mixing and dissolving the following ingredients. To this aqueous part (B), superposed electric waves of about 250 KHz were applied for 30 minutes.

| Aqueous part (B) | |
|---|---|
| Ingredient | Parts by weight |
| Sodium dl-pyrrolidonecarboxylate solution (50%) | 3.00 |
| Dipotassium glycyrrhetate | 0.10 |
| Paraoxybenzoate | 0.10 |
| Purified water (constant-pH oxygen-dissolved water) | 85.01 |
| Tartaric acid | 0.08 |
| Sodium hyaluronate | 0.01 |
| Human placental liquid | 0.20 |

(The total amount of the alcohol part (A) and the aqueous part (B) is 100 parts by weight.)

Then, the mixture of the parts (A) and (B) was kept stirred and superposed electric waves of about 500 KHz were applied to the stirred mixture for 30 minutes, to produce a lotion.

This lotion was tested for stability in the same manner as in Example 1. The results of this test were as shown in Table 2.

TABLE 2

| | Date of check | Evaluation of appearance | | | |
|---|---|---|---|---|---|
| | | pH value | Hue | Dispersion | Presence or absence of precipitate |
| Test at high temperature (for about six months) | October 1, 1985 | 5.50 | | | absence |
| | October 15, 1985 | 5.65 | | | " |
| | November 2, 1985 | 5.65 | | | " |
| | November 16, 1985 | 5.63 | | | " |
| | December 2, 1985 | 5.70 | | | " |
| | December 16, 1985 | 5.75 | | | " |
| | January 7, 1986 | 5.80 | | | " |
| | February 5, 1986 | 5.81 | | | " |
| | March 3, 1986 | 5.80 | | | " |
| | March 31, 1986 | 5.80 | | | " |
| Test at low temperature (for about 2.5 months) | October 2, 1985 | 5.50 | | | " |
| | October 15, 1985 | 5.55 | | | " |
| | November 2, 1985 | 5.65 | | | " |
| | November 16, 1985 | 5.65 | | | " |
| | December 16, 1985 | 5.70 | | | " |

It is clearly noted from the test results given above that the lotion of this example, during about six month's standing, showed absolutely no sign of abnormality such as precipitation, indicating that the cosmetic lotion was uniform and stable for a long time.

The superposed electric waves which are used in the present invention are also highly useful for converting a strong aroma such as French perfume into a mild aroma. Even when a perfume of strong scent is contained, therefore, the cosmetics such as lotions, milky lotions and creams which are produced by the method of the present invention, have an advantage that they emit a mild aroma.

It will be understood that the procedure and materials for carrying out the method of this invention, the type, layout, and operational manner of the apparatus for working the method of this invention, and the type, capacity, and the like of the superposed electric wave oscillating device which have been described and illustrated herein above for the explanation of this invention may be modified and altered in various ways without departing from the spirit and scope of this invention as set forth in the appended claims.

What is claimed is:

1. A method for the production of a cosmetic, which comprises applying superposed electric waves severally on an aqueous part and an alcohol part or an oil part, then mixing said aqueous part with said alcohol part and/or said oil part, and subsequently applying superposed electric waves again on the resultant mixture, wherein the aqueous part is an aqueous solution having water as a main component thereof, the alcohol part and the oil part are mixtures having an alcohol and an oil respectively as a main component thereof and incorporating therein additives for said cosmetic, and the superposed electric waves are superposed waves obtained by superposing a high-frequency electric current or medium to long wavelength on a high-frequency electric current of short wavelength.

2. A method according to claim 1, wherein said superposed electric waves are those formed by superposing medium to long electric waves of 100 to 3,000 KHz on short electric waves of 25 to 30 MHz.

3. A method according to claim 1, wherein said superposed electric waves are those formed by superposing medium electric waves of 250 to 500 KHz on short electric waves of 25 to 30 MHz.

4. A method according to claim 1, wherein said superposed electric waves are applied for a period approximately in the range of 5 to 100 minutes per Kg of the aqueous part, the alcohol part, the oil part, or the mixture thereof.

5. A method according to claim 1, wherein said water in said aqueous part is a deionized water.

6. A method according to claim 1, wherein said water in said aqueous part is a constant-pH water obtained by causing a purified water obtained by treating a water with an ion-exchange resin and/or activated carbon to absorb ozone-containing air obtained by passing the air through a high-voltage electron discharge device, said constant-pH water possessing a pH value approximately in the range of 7.5 to 8.0 and a dissolved oxygen content approximately in the range of 8 to 11 ppm.

7. A method according to claim 1, wherein said alcohol in said alcohol part is ethanol.

8. A method according to claim 1, wherein oil contained in said oil part is a vegetable oil, animal fat, mineral oil, or a fatty acid.

9. A method according to claim 1, wherein said additives for a cosmetic are selected from among a perfume, a dye, antiseptics, an antioxidant, a thickening agent, an allergy-mitigating agent, a humectant, and animal and vegetable extracts.

10. A method according to claim 1, wherein a cosmetic lotion is produced by combining 94 to 80 parts by weight of an aqueous part and 6 to 20 parts by weight of an alcohol part containing an oil in a ratio in the range of 1 to 10% by weight, based on the total amount of said cosmetic lotion.

11. A method according to claim 1, wherein a cosmetic milky solution is produced by combining 80 to 90 parts by weight of an aqueous part and 20 to 10 parts by weight of an oil part, based on the total amount of said milky solution.

12. A method according to claim 1, wherein a cosmetic cream is produced by combining 50 to 70 parts by weight of an aqueous part and 50 to 30 parts by weight of an oil part, based on the total amount of said cosmetic cream.

* * * * *